United States Patent [19]

McIntyre

[11] Patent Number: 5,202,359
[45] Date of Patent: Apr. 13, 1993

[54] PHOTOINITIATORS THAT ARE SOLUBLE IN HIGHLY FLUORINATED MONOMERS

[75] Inventor: Daniel K. McIntyre, St. Paul, Minn.

[73] Assignee: Minnesota Mining and Manufacturing Company, St. Paul, Minn.

[21] Appl. No.: 525,154

[22] Filed: May 17, 1990

[51] Int. Cl.$^5$ .............................................. C08G 2/46
[52] U.S. Cl. ...................................... 522/44; 522/40; 522/46
[58] Field of Search ........................... 522/44, 40, 46

[56] References Cited

U.S. PATENT DOCUMENTS

| | | | |
|---|---|---|---|
| 2,732,398 | 1/1956 | Brice et al. | 260/503 |
| 3,250,807 | 5/1966 | Fritz et al. | 260/535 |
| 3,250,808 | 5/1966 | Moore, Jr. et al. | 260/535 |
| 3,346,612 | 10/1967 | Hansen | 260/456 |
| 3,398,182 | 8/1968 | Geunthner et al. | 260/455 |
| 3,505,229 | 4/1970 | Skehan | 252/54 |
| 3,699,145 | 10/1972 | Sianesi et al. | 260/463 |
| 3,810,874 | 5/1974 | Mitsch et al. | 260/75 H |
| 3,810,875 | 5/1974 | Rice et al. | 260/899 |
| 3,814,741 | 6/1974 | Caporiccio et al. | 260/86.1 E |
| 3,882,193 | 5/1975 | Rice et al. | 260/874 |
| 3,896,167 | 7/1975 | Sianesi et al. | 260/544 F |
| 3,916,053 | 10/1975 | Sherman et al. | 428/96 |
| 4,170,636 | 10/1979 | Engel et al. | 424/52 |
| 4,321,404 | 3/1982 | Williams et al. | 560/115 |
| 4,347,111 | 8/1982 | Gehlhaus et al. | 522/42 |
| 4,472,480 | 9/1984 | Olson | 428/332 |
| 4,743,300 | 5/1988 | Brinduse et al. | 106/38.22 |

FOREIGN PATENT DOCUMENTS

OS2653601 6/1978 Fed. Rep. of Germany.
DE34214-71A1 12/1985 Fed. Rep. of Germany.

OTHER PUBLICATIONS

Hult and Ranby, Polymer Preprints, vol. 25 (1), 329 (1984) *J. Org. Chem.*, 48, p. 987 (1983).
Zh. Obsch. Khim. 34, 2974 (1964).

*Primary Examiner*—Marion E. McCamish
*Assistant Examiner*—Mark A. Chapman
*Attorney, Agent, or Firm*—Gary L. Griswold; Walter N. Kirn; David L. Weinstein

[57] ABSTRACT

Highly fluorinated alkyl group substituted acetophenones and benzophenones suitable for use as initiators for the polymerization of ethylenically-unsaturated monomers in which conventional initiators have limited solubility. These compounds are particularly suitable for use for the polymerization of highly fluorinated ethylenically-unsaturated monomers.

17 Claims, No Drawings

PHOTOINITIATORS THAT ARE SOLUBLE IN HIGHLY FLUORINATED MONOMERS

BACKGROUND OF THE INVENTION

1. Field of the Invention

This invention relates to photoinitiators for the polymerization of free radically-polymerizable compounds. In particular, the invention relates to fluorine-containing photoinitiators that are soluble in free radically-polymerizable compounds in which conventional photoinitiators are not soluble.

2. Discussion of the Art

It has long been known that ethylenically-unsaturated compounds, particularly ethenyl and isopropenyl group-containing monomers, can be polymerized by contacting them under polymerizing conditions in the presence of compounds that generate free radicals on application of heat or actinic radiation. Compounds that are capable of generating free radicals include dialkoxyacetophenones, hydroxyacetophenones, diarylacetophenones, chlorinated acetophenones, benzophenones, benzoin ethers, benzoins, benzils, benzildialkylketals, α-acyloxime esters, fluorenones, xanthones, and thioxanthones. These compounds can be substituted by various groups, including, for example, alkyl, alkoxy, and hydroxy groups. Although these compounds are useful for many purposes where the generation of free radicals is necessary, such as the polymerization of ethylenically-unsaturated monomers, their poor solubility in highly fluorinated monomers limits their use in these monomers.

U.S. Pat. No. 3,896,167 discloses peroxidic perfluoropolyethers that are soluble in highly fluorinated ethylenically-unsaturated monomers; however, these compounds are explosive and should be handled behind barricades.

U.S. Pat. No. 4,170,636 discloses perfluoroalkyl substituted aromatic compounds having a calcium-complexing moiety for use in dentifrice compositions. Among the disclosed compounds is the following compound:

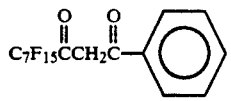

Hutt and Ranby, Polymer Preprints, Vol. 25(1), 329 (1984) disclose the use of the following perfluorosulfonamido substituted acetophenone compound as a surface active photoinitiator useful in combination with a common initiator for photocuring (crosslinking) acrylic resins in air:

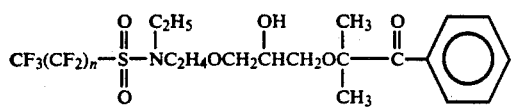

Deutsches Offenlegungsschrift 2653601 discloses hydroxyketones having the general formula:

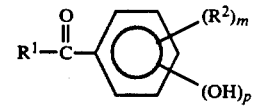

wherein $R^1$ can be an aryl group substituted by a perfluoroalkyl group, $R^2$ is hydrogen or a perfluoroalkyl group of 1 to 5 carbon atoms, m and p are independently 1 or 2, there being at least one perfluoroalkyl group in the compound. The compounds are useful as dyestuff intermediates and plant protection agents.

Accordingly, there is a need for initiators for the photopolymerization of systems that contain ethylenically-unsaturated monomers in which conventional photoinitiators are not soluble.

SUMMARY OF THE INVENTION

The present invention provides compounds that are suitable for use as initiators for photopolymerization of polymerizable systems that contain ethylenically-unsaturated monomers in which conventional photoinitiators have limited solubility, if any. The initiators of the present invention are particularly suitable for use with highly fluorinated ethylenically-unsaturated monomers.

The compounds of the present invention are phenolic hydroxyl free acetophenones and benzophenones in which at least one aryl group is substituted by a polyfluoroaliphatic group. The compounds of the invention have the general structural formula:

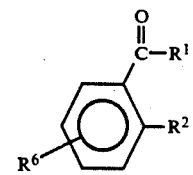

wherein
$R^1$ represents

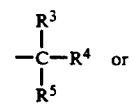

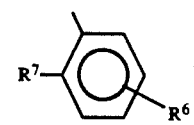

each $R^3$, $R^4$, and $R^5$ independently represents a member selected from the group consisting of hydrogen, halogen, hydroxy, alkyl group, alkoxy group, and phenyl group, provided that at least one of $R^3$, $R^4$, or $R^5$ is selected from the group consisting of halogen, hydroxy, and alkoxy group, or any two of $R^3$, $R^4$, and $R^5$ together represent a straight-chain or branched-chained alkylene group, preferably having four to eight carbon atoms, that forms, along with the carbon atoms to which they are attached a 5- or 6- membered carbocyclic ring, or any two of $R^3$, $R^4$, and $R^5$ together represent carbonyl oxygen, provided that the remaining $R^3$, $R^4$, or $R^5$ is selected from the group consisting of halogen, hydroxy, and alkoxy group;

each of $R^2$ and $R^7$ independently represents a member selected from the group consisting of hydrogen, halogen, and lower alkyl group having one to six carbon atoms, or $R^2$ and $R^7$ together represent a coordinate bond, an oxygen atom, or a sulfur atom joining the phenyl group of Formula I to the phenyl group of the moiety of Formula III;

each $R^6$ group independently represents a member selected from the group consisting of hydrogen, lower alkyl group having one to six carbon atoms, and polyfluoroaliphatic group, $-XR_fY$, in which X represents a polyvalent group joining $-R_fY$ to a group of Formula I or a phenyl group of the moieties of Formula II or Formula III, $R_f$ represents either (1) a polyfluorinated, saturated, divalent aliphatic group, preferably having 4 to 24 carbon atoms, that is straight-chain, branched, or cyclic and contains no more than one hydrogen atom per four fluorine atoms or (2) a divalent poly(fluorooxyalkylene) group having a number average molecular weight of from about 200 to 20,000 or higher, preferably 500 to 1,000, and Y represents a fluorine atom or X, provided that when Y represents X the divalent group $-XR_fX-$ joins two phenyl groups of Formula I, provided that at least one of the $R^6$ groups is $XR_fY$.

DETAILED DESCRIPTION OF THE INVENTION

The photoinitiators of the invention can be further depicted by the structural formulas:

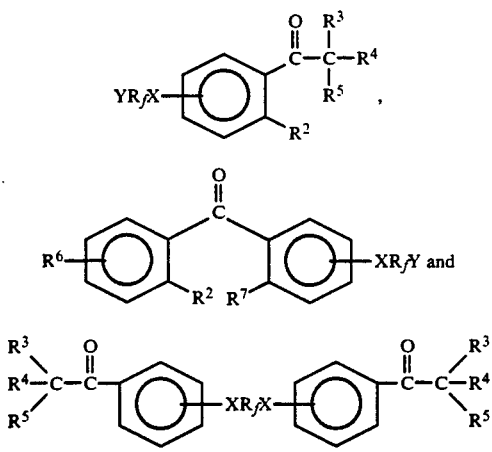

in which $R^2$, $R^3$, $R^4$, $R^5$, $R^6$, $R^7$ and $R_f$ are as described previously.

Alkyl groups represented by $R^3$, $R^4$, and $R^5$ can be saturated or unsaturated, linear, branched, or cyclic. The alkyl groups preferably contain from one to six carbon atoms The alkyl groups can be unsubstituted or substituted. Representative examples of unsubstituted alkyl groups include the following: methyl, ethyl, n-propyl, isopropyl, n-butyl, n-pentyl, 2-ethylpropyl, n-hexyl, cyclopentyl, methylcyclopentyl, and cyclohexyl. If substituted, the substituents should be of sufficiently low polarity that they do not adversely affect solubility of the compound in highly fluorinated monomers. Representative examples of substituents for the alkyl groups include halogens and alkoxy groups having one to six carbon atoms. Representative examples of halogen substituted alkyl groups include chloromethyl, trichloromethyl, and pentachloroethyl. Representative examples of alkoxy substituted alkyl groups include methoxyethyl, ethoxyethyl, and propoxypropyl.

Alkoxy groups represented by $R^3$, $R^4$, and $R^5$ preferably contain from one to six carbon atoms. The alkoxy groups can be unsubstituted or substituted. Representative examples of unsubstituted alkoxy groups represented by $R^3$, $R^4$, and $R^5$ include methoxy, ethoxy, butoxy, cyclohexoxy. If substituted, the substituents should be of sufficiently low polarity that they do not adversely affect solubility of the compound in highly fluorinated monomers. Representative examples of suitable substituents for the alkoxy groups include halogens and alkoxy groups having one to six carbon atoms.

If $R^3$, $R^4$, or $R^5$ is a phenyl group, it can be unsubstituted or substituted. If substituted, the substituents should be of sufficiently low polarity that they do not adversely affect solubility of the compound in highly fluorinated monomers. For example, aminophenyl groups and hydroxyphenyl groups would not be acceptable as substituted phenyl groups. Representative examples of phenyl groups represented by $R^3$, $R^4$, and $R^5$ include the following groups: unsubstituted phenyl, halophenyl, such as chlorophenyl, bromophenyl, or iodophenyl; alkylphenyl, where the alkyl group has one to six carbon atoms, such as tolyl or ethylphenyl; alkoxyphenyl, where the alkoxy group has one to six carbon atoms, such as methoxyphenyl; or an $R^6$ group-substituted phenyl, where $R^6$ is as described previously.

Where any two of $R^3$, $R^4$, and $R^5$ together represent an alkylene group, there can be formed with the carbon atom to which they are attached cycloalkyl groups, such as, for example, a cyclopentyl group, a cyclohexyl group, a methylcyclopentyl group, or an ethylcyclohexyl group. These alkylene groups can be substituted with substituents of sufficiently low polarity that they do not adversely affect solubility of the compound in highly fluorinated monomers.

Representative examples of lower alkyl groups represented by $R^2$ and $R^7$ include the following groups: methyl, ethyl, isopropyl, n-butyl, and t-butyl.

The polyfluorinated aliphatic group, $R_f$, of the photoinitiator of this invention is stable, inert, and non-polar. It can be straight chain, branched chain, and, if sufficiently large, cyclic, or combinations thereof, such as an alkylcycloaliphatic radical. The skeletal chain can include catenary oxygen or trivalent nitrogen hetero atoms, or both, bonded only to carbon atoms, such hetero atoms providing stable linkages between fluorocarbon groups and not interfering with the inert character of the $R_f$ radical. While $R_f$ can have a large number of carbon atoms, compounds where $R_f$ is not more than 24 carbon atoms are preferred, since large radicals usually represent a less efficient utilization of fluorine than is possible with smaller $R_f$ radicals. Generally, $R_fY$, in which Y is fluorine, will have 4 to 20 carbon atoms, preferably 6 to 12, and will contain 40 to 78 percent by weight, preferably 50 to 78 percent by weight of fluorine. The terminal portion of the $R_fY$ group preferably has at least three fully fluorinated carbon atoms, e.g., $CF_3CF_2CF_2-$, and the preferred photoinitiators are those in which the $R_fY$ group is completely or substantially completely fluorinated, as in the case where $R_fY$ is perfluoroalkyl, $C_nF_{2n+1}$, and perfluoroalkylalkyl, $C_nF_{2n+1}CH_2-$ and $C_nF_{2n+1}CH_2CH_2-$, in which n is 4 to 20. Examples of hydrogen-containing $R_fY$ groups include the undecafluoro-1,1-dihydrohexyl, pentadecafluoro-1,1-dihydrooctyl, tricosafluoro-1,1-dihydrododecyl, and pentadecafluoro-1,1,2,2-tetrahydrooctyl groups.

Where $R_f$ is a divalent poly(fluorooxyalkylene) group, it has randomly distributed units selected from —$CF_2O$—, —$CF_2CF_2O$— and —$C_3F_6O$—, and it may also have incorporated therein such group as the following:

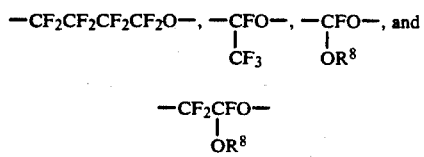

wherein $R^8$ represents a perfluoroalkyl group or a perfluoroalkyl group substituted by one or more ether oxygen atoms. Examples of such $R_f$ groups are disclosed in U.S. Pat. Nos. 3,250,807; 3,250,808; 3,505,229; 3,699,145; 3,810,874; 3,810,875; 3,814,741; 3,882,193; and 4,743,300, which patents are incorporated herein by reference.

The connecting group, X, can be any of the polyvalent, preferably divalent, connecting groups known for connecting a polyfluoroalkyl or poly(fluorooxyalkylene) group to organic moieties. Examples of connecting groups preferred for this invention include:

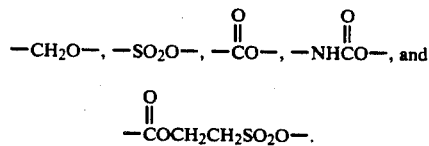

Examples of other connecting groups suitable for this invention include:

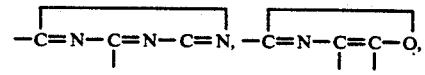

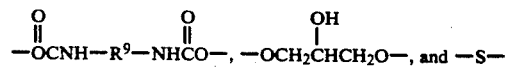

wherein $R^9$ represents a divalent alkylene group having 1 to 6 carbon atoms or one or more divalent phenyl groups.

Still other groups are disclosed in U.S. Pat. Nos. 3,810,874 and 3,398,182.

The compounds of this invention can be prepared by various methods. Compounds of Formula I in which X is —$SO_2O$— can be prepared by reaction of the corresponding phenolic acetophenone and benzophenone compounds with a polyfluoroalkylsulfonyl fluoride as shown in the following exemplary schemes:

Scheme 1

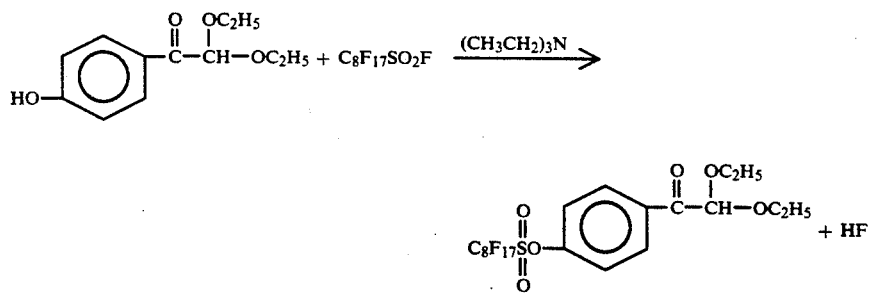

Scheme 2

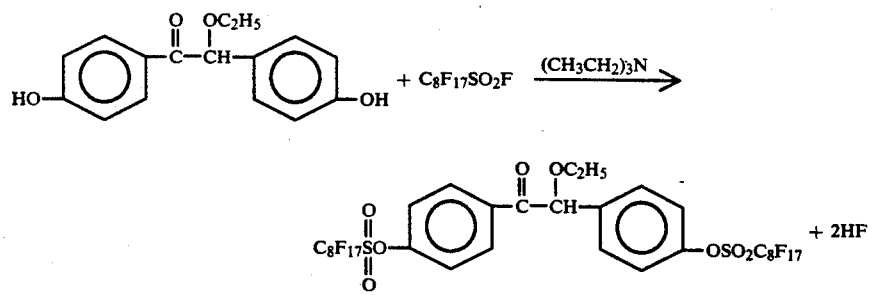

Scheme 3

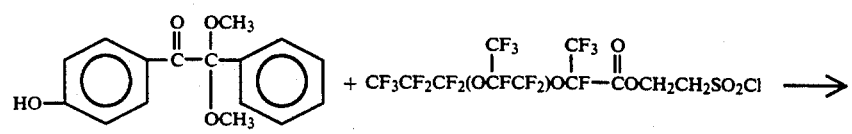

-continued

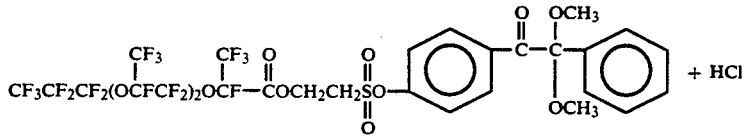

The reaction can be performed in accordance with procedures described in U.S. Pat. Nos. 2,732,398 and 3,346,612 by heating the phenolic compound with the polyfluoroalkylsulfonyl fluoride in the presence of a strong base such as the trialkylamines, N-lower alkyl piperidines, alkali metal phenoxides, and the like.

Examples of polyfluoroaliphatic group-substituted photoinitiators of the invention in which X is —SO₂O— are:

2-methoxy-1-(4-perfluorbutylsulfonyloxy)phenyl-1-

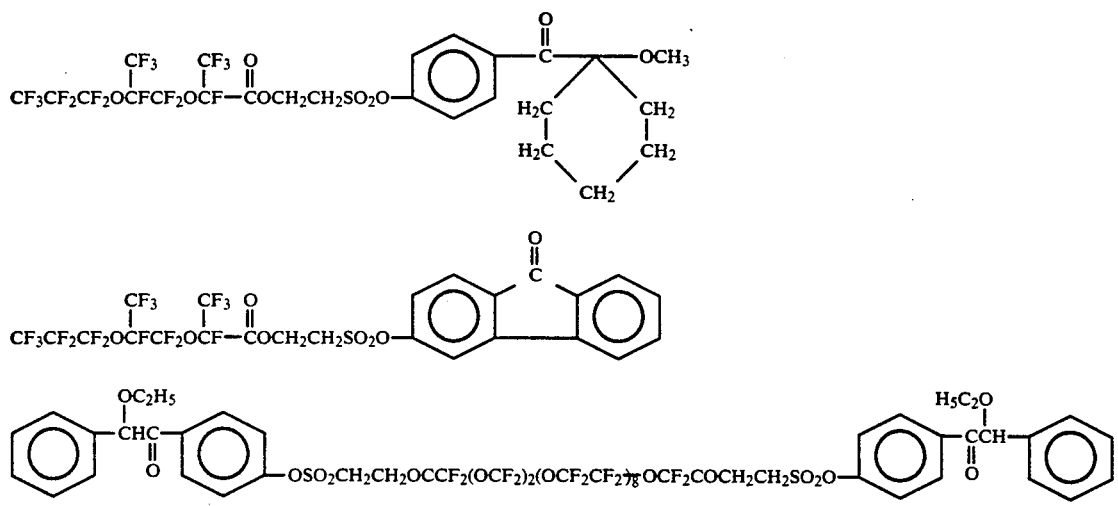

ethanone
2,2-dimethoxy-1-(4-perfluorohexylsulfonyloxy)phenyl-1-ethanone
2-ethoxy-1-(4-perfluorooctylsulfonyloxy)phenyl-1-ethanone
2-(2-chloroethoxy)-1-(4-perfluorooctylsulfonyloxy)-phenyl-1-ethanone
2,2-dimethyl-1-(4-perfluorohexylsulfonyloxy)phenyl-1-ethanone
2-ethoxy-1-(2-methyl-4-perfluorooctylsulfonyloxy)phenyl-1-ethanone
2-ethoxy-1-(2,6-di-t-butyl-4-perfluorododecylsulfonyloxy)phenyl-1-ethanone
2-chloro-1-(4-perfluorooctylsulfonyloxy)phenyl-1-ethanone
2,2,2-trichloro-1-(4-perfluorooctylsulfonyloxy)phenyl-1-ethanone
2-ethoxy-1-(4-perfluorooctylsulfonyloxy(phenyl-2-phenyl-1-ethanone
2-ethoxy-1,2-bis[(4-perfluorooctylsulfonyloxy)phenyl]-1-ethanone
2-[(2-ethoxy)ethoxy]-1-(4-perfluorohexylsulfonyloxy)-phenyl-2-phenyl-1-ethanone
1,1-bis[4-perfluorooctylsulfonyloxy)phenyl]methanone
1,1-bis[4-(1,1-dihydropentadecafluorooctylsulfonyloxy)phenyl]methanone
cyclohexyl(4-perfluorooctylsulfonyloxyphenyl)methanone
cyclopentyl(4-perfluorooctylsulfonyloxyphenyl)methanone
(4-perfluorooctylsulfonyloxylphenyl)phenylmethanone
4-perfluorooctylsulfonyloxyfluoroenone
3,6-bis(4-perfluorooctylsulfonyloxy)fluorene
4-perfluorododecylsulfonyloxyxanthone
4-perfluorodecylsulfonyloxythioxanthone
2-ethoxy-1-[4-(1,1-dihydropentadecafluorooctylsulfonyloxy)-phenyl]-2-phenyl-1-ethanone
2,2-diethoxy-1,2-bis[4-1,1-dihydroundecafluorohexylsulfonyloxy)-phenyl]-1-ethanone Compounds of Formula I in which X is

can be prepared from the corresponding phenolic compounds in accordance with the disclosures in Zh. Obsch. Khim. 34, 2974 (1964) and DE 3,421,471 by reaction of these compounds with polyfluoroalkylcarbonyl halide in the presence of a base such as an alkali metal hydroxide or a tertiary amine as shown in the following exemplary schemes:

Scheme 4

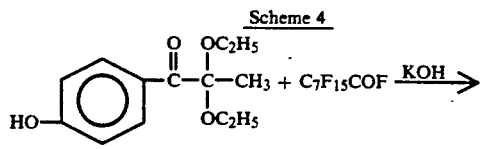

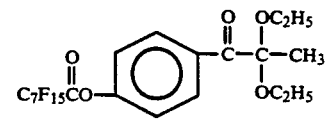

Scheme 5

-continued

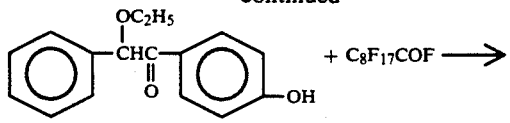

Examples of polyfluoroaliphatic group-substituted photoinitiators in which X is $$-O\overset{O}{\underset{\|}{C}}-$$

include:

2-ethoxy-1-(4-perfluorooctanoyloxy)phenyl-1-ethanone
2-ethxoy-1,2-bis(4-perfluorooctanoyloxy)phenyl-1-ethanone
4-perfluorododecanoyloxyxanthone
2,2,2-trichloro-1-(4-perfluorooctanoyloxy)Phenyl-1-ethanone
2,2-dimethoxy-1,2-bis[(1-4-perfluorohexanoyloxy)phenyl-1-ethanone

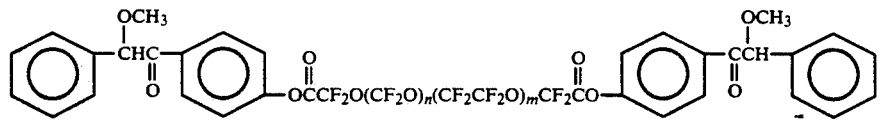

wherein m and n have independent values. For example, the values of m and n can range from 1 to 200 and the ratio m to n can range from 0.2 to 1 to 5 to 1.

Compounds of Formula I in which X is —NHCO— can be prepared from the corresponding phenolic acetophenone and benzophenone compounds by reaction of these compounds with a polyfluorinated aliphatic isocyanate, described in U.S. Pat. No. 3,810,874, as shown in the following exemplary schemes:

Scheme 6

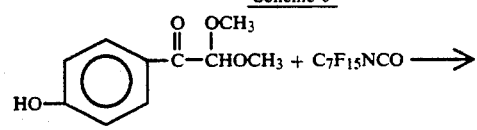

-continued

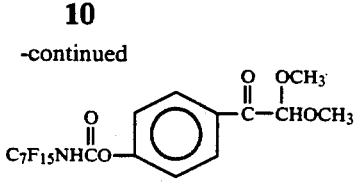

Scheme 7

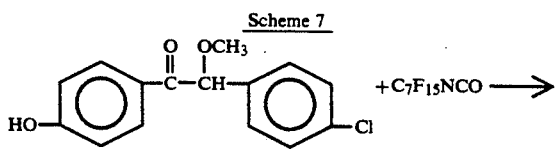

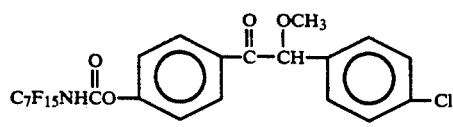

Scheme 8

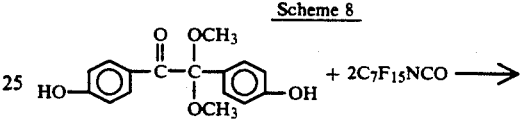

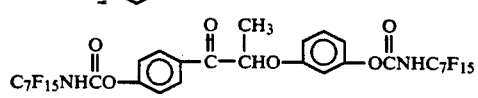

Scheme 9

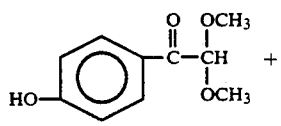

OCNCH$_2$CF$_2$(OCF$_2$CF$_2$)$_8$(OCF$_2$)$_2$OCF$_2$CH$_2$NCO $\longrightarrow$

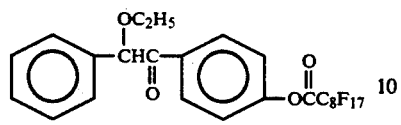

Compounds of Formula I in which X is —CH$_3$O can be prepared from corresponding phenolic acetophenone and benzophenone compounds by reaction of these compounds with a perfluoroalkane sulfonate ester of a polyfluorinated aliphatic carbinol, as shown in the following scheme:

Scheme 10

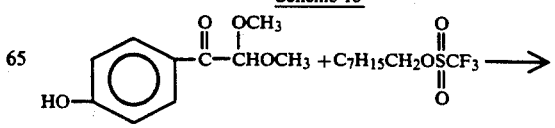

-continued
Scheme 10

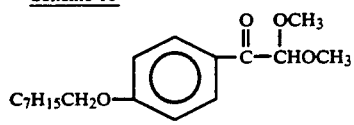

The compounds of this invention can be used as a photoinitiator for the polymerization of any monomeric compound that can be polymerized by free radical polymerization, particularly ethylenically-unsaturated compounds. The polyfluoroaliphatic group-substituted photoinitiators of this invention are especially useful for the polymerization of compounds by free radical polymerization in compositions in which conventional photoinitiators are not soluble, particularly compositions containing ethylenically-unsaturated fluorocarbon compounds. Included among these ethylenically-unsaturated fluorocarbon compounds are the polyfluoroalkyl monoacrylates, polyfluoroalkyldiacrylates and polyfluoroalkylmethacrylates such as, for example:

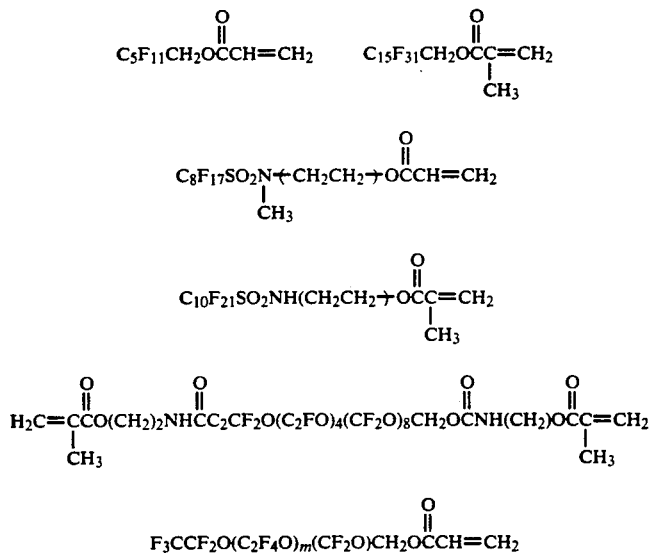

wherein m and n are defined above

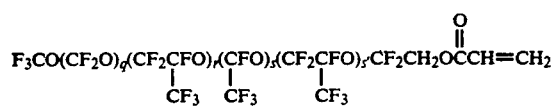

wherein q/r is 0.15, (s+s')/(q+r) is 0.07 and $M_n$=2450

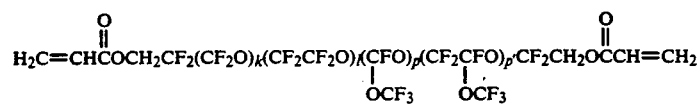

k/l is 1.48, (p+p')/(k+1) is 0.87 and p/p' is 1.87.

Other acrylates and methacrylates that can be used are disclosed in U.S. Pat. Nos. 3,916,053; 4,321,404; and 4,743,300, incorporated herein by reference.

Generally the photoinitiators of this invention can be used in an amount of about 0.01 to 10 parts, preferably about 0.1 to 5 parts, per 100 parts by weight of polymerizable monomer in a photopolymerizable system.

The photopolymerizable compositions of this invention can be readily prepared by introducing the photoinitiator in the desired amount into a composition containing one or a mixture of two or more polymerizable ethylenically-unsaturated compounds. Pigments, carriers, fillers, and thixotropic agents, such as glass fibers, beads, and bubbles, synthetic fibers, silica, and the like can be added. Up to 100 percent or more of these additives, based on weight of fluorocarbon, can be added as long as they do not interfere with the polymerizing radiation.

Radiation suitable for effecting polymerization of the composition typically ranges from about 200 to about 500 nm. The radiation can be from sunlight or it can be produced artificially as, for example, by mercury vapor lamps, xenon lamps, or tungsten lamps.

The photopolymerizable compositions of this invention can be polymerized, in situ, on a substrate to provide the substrate with a coating having a high degree of adhesion, and a high degree of resistance to water, oil, and soil.

Substrates that are suitable for bearing the photopolymerizable compositions of this invention include, for example, paper, glass, metals, such as steel and aluminum, polymers, such as polyester, polyvinylchloride, polyethylene, and polypropylene, woven and non-woven fabrics, and the like.

The invention is further illustrated by the following non-limiting examples, in which all parts are parts by weight, unless otherwise indicated.

EXAMPLE 1

Preparation of
2-ethoxy-1,2-bis[4-perfluorooctylsulfonyloxy)phenyl]-1-ethanone

2-Ethoxy-1,2-bis(4-hydroxyphenyl)ethane was derived from 4,4'-dihydroxybenzoin, which was prepared by the method disclosed in *J. Org. Chem.*, 48, p. 987 (1983), by first protecting the phenolic hydroxyl groups of 4,4'-dihydroxybenzoin by reaction with methane sulfonyl chloride to form the bis-methyl sulfonate ester of 4,4'-dihydroxybenzoin. The intermediate bis-methyl sulfonate ester was further reacted with acidic ethanol to form the benzoin ethyl ether. The methyl sulfonate groups were then cleaved by reaction with 1N aqueous sodium hydroxide to yield 2-ethoxy-1,2-bis(4-hydroxyphenyl)ethanone, which was separated from aqueous solution at pH of 7 by extraction with ethyl acetate and purified by recrystallization from methylene chloride.

A flask containing 1.0 g (0.0037 mole) of 2-ethoxy-1,2-bis(4-hydroxyphenyl)ethanone dissolved in a mixture of 20 ml triethylamine and 4 ml pyridine was heated under a nitrogen atmosphere to 90° C. To the flask was added, by syringe, 5.57 g (about 0.011 mole) of perfluorooctylsulfonyl fluoride that had been stabilized by refluxing 10 parts thereof with about 1 part each of anhydrous triethylamine and pyridine, separating the bases, and distilling. The mixture of the ethanone and the fluoride was heated at 90° C. for 1 ½ hours to form a homogeneous solution that was reddish in color. This solution was poured over ice contained in a 10% aqueous hydrogen chloride solution. The resulting aqueous solution was decanted from the solid product, and the solid was taken up in about 25 ml of 1,1,2-trichloro-1,2,2-trifluoroethane ("Freon TF", available from E.I. du Pont de Nemours and Company). The resulting solution was washed with equal volumes each of 10% HCl, saturated NaCl solution, 5M sodium hydroxide, and again with 5M sodium hydroxide. The washed solution was then dried with magnesium sulfate and attapulgus clay ("Attasorb Clay", available from Engelhard Corporation). The dried solution was filtered and then concentrated to a pasty solid that was dissolved in 50 ml of perfluorinated alkane solvent ("FC-77", available from Minnesota Mining and Manufacturing Company). This solution was stirred with magnesium sulfate and attapulgus clay, filtered, and concentrated to yield about 2 g of solid having a melting point of 50° C. Fluorine nuclear magnetic resonance ($^{19}$F NMR) indicated the solid to possess $C_8F_{17}SO_2O$ groups of which about 80% were linear and about 20% were branched.

The compound of Example 1 (40 mg) was dissolved in 2.0 g of a polyfluoropolyether diacrylate having the average structural formula:

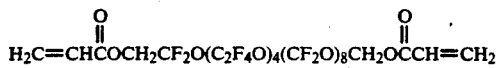

The solution placed in a test tube that had been flushed with nitrogen and then exposed to the radiation from a medium pressure Hanovia lamp at a distance of about 5 cm for about one minute. A clear firm rubber button was obtained.

EXAMPLE 2

Preparation of
1,1-bis[4-(perfluorooctylsulfonyloxy)phenyl]methanone

A 100 ml flask containing 2.0 g (0.009 mole) of bis(4-hydroxyphenyl)methanone dissolved in a mixture of 20 ml of triethylamine and 10 ml pyridine was heated in an oil bath to 90° C. To the solution was then added stabilized perfluorooctylsulfonyl fluoride (11.2 g, 0.022 mole) and the reaction mixture stirred for 2½ hours at 90° C. The mixture was cooled and poured over ice in a beaker containing 200 ml 10% aqueous hydrogen chloride solution (HCl). A solid cake formed, which was taken up with 200 ml 1,1,2-trichloro-1,2,2-trifluoroethane ("Freon TF", available from E.I. du Pont de Nemours and Company). The aqueous phase was separated and the resulting solution was washed with equal volumes (100 ml) 10% aqueous hydrochloric acid, dilute hydrochloric acid (1%), and finally with 10% aqueous sodium bicarbonate. It was then treated with $MgSO_4$ and carbon. The resulting yellow solution was filtered and concentrated to give 7 g of solid, which was triturated with 100 ml of a perfluoroalkane solvent ("FC-75", available from Minnesota Mining and Manufacturing Company). Filtration of the yellow solution gave 2.5 g of white solid which was characterized by $^1$H and $^{19}$F NMR analysis to be the desired product, which had a melting point of 139-143° C. Concentration of the filtrate gave about 5 g of a yellow waxy solid. NMR spectroscopy indicated that the yellow waxy solid had enriched branching in the perfluorooctyl chains.

Polyfluoropolyether diacrylate was polymerized using both the desired product and the product with enriched branching to give clear firm rubber buttons.

EXAMPLE 3

Preparation of
1,1-bis[4-(1,1-dihydropentadecafluorooctyloxy)-phenyl]methanone

Into a flask containing 10 ml of dimethylformamide was added 0.5 g (0.002 mole) 1,1-bis (4-hydroxyphenyl)-methanone, 0.1 g tetrabutylammonium bromide, and 0.34 g crushed potassium hydroxide. The mixture was stirred until the base dissolved. Then, 1,1-alihydropentadecafluorooctyl trifluoromethanesulfonate (2.73 g, 0.005 mole) was added. A solution having a reddish color formed. This solution was heated overnight in an oil bath at 60° C., where upon its color faded to a golden yellow. The reaction mixture was cooled and poured into water. A solid precipitate formed. The precipitate was taken up with 1,1,2-trichloro-1,2,2-trifluoroethane ("Freon TF", available from E.I. du Pont de Nemours and Company) (100 ml), washed with water, and dried over $MgSO_4$ and carbon. The dried solution was filtered and concentrated to a pale amber colored solid, which was triturated with 100 ml of a perfluoroalkane solvent ("FC-75", available from Minnesota Mining and Manufacturing Company). Some material did not dissolve. The mixture was filtered to yield 0.4 g white solid having a melting point of 119-122° C. and characterized by $^1$H NMR and $^{19}$F NMR as the product. Concentration of the 100 ml of a perfluoroalkane solvent ("FC-75", available from Minnesota Mining and Manufacturing Company) filtrate gave 0.6 g of pale yellow waxy solid that melted over a broad temperature range of from 55 to 72° C. This material had a higher percentage of branching in the perfluoroalkyl group than the product melting at 119-122° C.

Two percent solutions of each of the products of Example 2 were prepared in a poly(perfluoropropyleneoxy) oligomer having the formula:

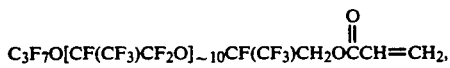

and each solution diluted with 100 ml of a perfluoroalkane solvent ("FC-75", available from Minnesota Mining and Manufacturing Company) to form a 10% solution. The poly(perfluoropropyleneoxy) oligomer having the formula:

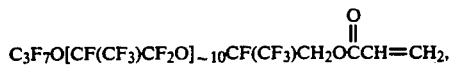

was prepared by reducing poly(perfluoropropyleneoxy) carboxylic acid having a number average molecular weight of about 2,000 ("Krytox 157 FS", available from E.I. du Pont de Nemours and Company) to poly(fluoropropyleneoxy) carbinol and then esterifying the carbinol with acryloyl chloride Into each solution was dipped a polypropylene film and each coated film was exposed to ultraviolet radiation to cure the coating.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A phenolic hydroxyl free compound having the structural formula:

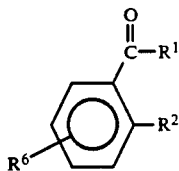   I wherein
$R^1$ represents

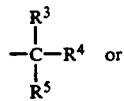   II

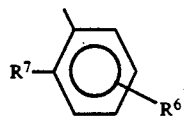   III wherein
each of $R^3$, $R^4$, and $R^5$ independently represents a member selected from the group consisting of hydrogen, halogen, hydroxy, alkyl group, alkoxy group, and phenyl group, provided that at least one of $R^3$, $R^4$, or $R^5$ is selected from the group consisting of halogen, hydroxy, and alkoxy group, or any two of $R^3$, $R^4$, and $R^5$ together represent a branched or unbranched alkylene group that forms together with the carbon atoms to which they are attached a 5- or 6-membered carbocyclic ring, or any two of $R^3$, $R^4$, and $R^5$ together represent carbonyl oxygen, provided that the remaining $R^3$, $R^4$, or $R^5$ is selected from the group consisting of halogen, hydroxy, alkoxy group, and phenyl group;

each of $R^2$ and $R^7$ independently represents a member selected from the group consisting of hydrogen, halogen, and lower alkyl group having one to six carbon atoms, or $R^2$ and $R^7$ together represent a coordinate bond, an oxygen atom, or a sulfur atom joining the phenyl group of Formula I to the phenyl group of the moiety of Formula III;

each $R^6$ group independently represents a member selected from the group consisting of hydrogen, lower alkyl group having 1 to 6 carbon atoms, and polyfluoroaliphatic group, $-XR_fY$, in which X represents a polyvalent connecting group joining $-R_fY$ to a phenyl group of Formula I or of a phenyl group of the moiety of Formula II or the moiety of Formula III, $R_f$ represents either (a) a polyfluorinated, saturated, divalent aliphatic group that is straight-chain, branched-chain, or cyclic, and contains no more than one hydrogen atom per four fluorine atoms, or (2) divalent poly(fluorooxyalkylene) group having a number average molecular weight of from about 200 to 20,000, and Y represents a fluorine atom or X, and when Y represents X, the divalent group-13 $XR_fX$—joins two phenyl groups of Formula I, provided that at least one of $R^6$ groups is $-XR_fY$ and said compound is soluble in ethylenically-unsaturated fluorocarbon compounds.

2. The compound of claim 1, wherein $R^3$, $R^4$, or $R^5$ represents an alkyl group having one to six carbon atoms.

3. The compound of claim 1, wherein $R^3$, $R^4$, or $R^5$ represents a haloalkyl group having one to six carbon atoms.

4. The compound of claim 1, wherein $R^3$, $R^4$, or $R^5$ represents a phenyl group.

5. The compound of claim 1, wherein $R^3$, $R^4$, or $R^5$ represents a substituted alkyl group, a substituted alkoxy group, or substituted phenyl group wherein the substituents are of sufficiently low polarity that they do not adversely affect solubility of the compound in highly fluorinated monomers.

6. The compound of claim 5, wherein said substituents are selected from the group consisting of halogens and alkoxy groups.

7. The compound of claim 1, wherein $R^3$, $R^4$, or $R^5$ represents an alkoxy group having one to six carbon atoms.

8. The compound of claim 1, wherein two of $R^3$, $R^4$, and $R^5$ represent an alkylene group having four to eight carbon atoms.

9. The compound of claim 1, wherein $R^6$ represents a divalent aliphatic group having 4 to 24 carbon atoms.

10. The compound of claim 1, selected from the group consisting of 2-ethoxy-1,2-bis[4-perfluorooctylsulfonyloxy)phenyl]-1-ethanone, 1,1-bis[4-(perfluorooctylsulfonyloxy)phenyl]methanone, 1,1-bis[4-1(1,1-dihydropentadecafluorooctyloxy)phenyl]methanone, 2,2-dimethoxy-1-[4-(perfluorohexylsulfonyloxy)phenyl]-1-ethanone, and

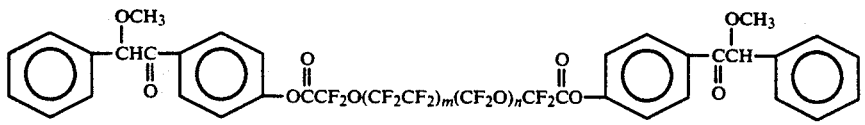

wherein m and n independently represent numbers ranging from 1 to 200 and the ratio of m to n ranges from 0.2 to 1 to 5 to 1.

11. A composition comprising a free radically polymerizable compound and a compound of claim 1.

12. A coated substrate comprising a substrate bearing thereon a layer of the composition of claim 11.

13. The coated substrate of claim 12, wherein the substrate is selected from the group consisting of paper, glass, metals, and polymers.

14. The compound of claim 1, wherein X represents a polyvalent group selected from the group consisting of:

$$-CH_2O-, -\overset{O}{\underset{\|}{C}}O-, -NH\overset{O}{\underset{\|}{C}}O-, -\overset{O}{\underset{\|}{C}}OCH_2CH_2SO_2O-,$$

-continued

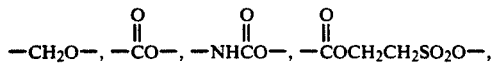

wherein $R^9$ represents a divalent alkylene group having 1 to 6 carbon atoms or one or more divalent phenyl groups.

15. A composition comprising a free radically polymerizable compound and a compound of claim 14.

16. A coated substrate comprising a substrate bearing thereon a layer of the composition of claim 15.

17. The coated substrate of claim 16, wherein the substrate is selected from the group consisting of paper, glass, metals, and polymers.

* * * * *

UNITED STATES PATENT AND TRADEMARK OFFICE
CERTIFICATE OF CORRECTION

PATENT NO. : 5,202,359
DATED : April 13, 1993
INVENTOR(S) : McIntyre

It is certified that error appears in the above-indentified patent and that said Letters Patent is hereby corrected as shown below:

Col. 11, line 46, should be:

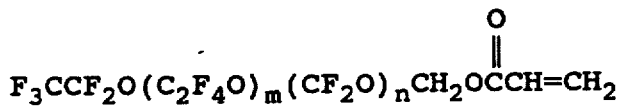

Col. 16, line 31, "group-13 $XR_fX$-joins" should be --group - $XR_fX$- joins--.

Col. 18, line 14, before "and -S-", insert:

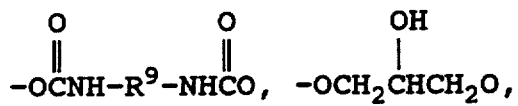

Signed and Sealed this

First Day of November, 1994

Attest:

BRUCE LEHMAN

Attesting Officer    Commissioner of Patents and Trademarks